United States Patent [19]

Barberet et al.

[11] Patent Number: Plant 5,446

[45] Date of Patent: Apr. 23, 1985

[54] CARNATION NAMED LONSICO

[75] Inventors: Nicole Barberet; Yves Ducloux, both of Antibes, France

[73] Assignee: Laboratoire de Physiologie Vegetale de La Londe, Antibes, France

[21] Appl. No.: 516,521

[22] Filed: Jul. 25, 1983

[51] Int. Cl.[3] ..... A01H 5/00

[52] U.S. Cl. ..... Plt./73

[58] Field of Search ..... Plt./70, 73

*Primary Examiner*—Robert E. Bagwill

*Attorney, Agent, or Firm*—Charles W. Rummler

[57] ABSTRACT

A new carnation variety particularly distinguished by the substantially solid ruby red coloration of its medium sized blooms which are borne on long, strong, straight stems and which bloom profusely during the recurrent blooming seasons of Spring and Fall, this plant having a vigorous, upright growth habit with rigid stems and comparatively few leaves, the plant height at eight months averaging about 100 cm.

1 Drawing Figure

BACKGROUND OF THE NEW PLANT

Our new carnation cultivar is the result of breeding efforts carried on by us at La Londe, Les Maures, France, since 1977, with the object of bringing about a strong plant of nice color and good quality of growth habit which would also be resistant to *Fusarium oxysporum*. This new plant originated as a seedling produced by our crossing of selected and individually identified carnations growing among our collection of distinctive plants maintained at La Londe for breeding purposes. This particular seedling was selected by us for propagation and test because of its solid ruby red appearance, its profuse production of flowers and its apparently favorable growth habit. The discovery plant was reproduced by us at La Londe by means of cuttings of the parent and the resulting propagation appearing to be very favorable with respect to retention of the novel characteristics of the parent, we continued the propagation of this plant through several successive generations and thereby established that the novel and distinctive characteristics of the discovery plant were fully retained from generation to generation and appeared to be firmly fixed.

DESCRIPTION OF THE DRAWING

Our new carnaton cultivar is illustrated by the accompanying photographic drawing which shows, in full color, a typical arrangement of buds and flowers in various stages of opening, the colors shown being as nearly true to those specified herein as is reasonably possible to obtain by conventional photographic procedures.

DESCRIPTION OF THE NEW PLANT

The following is a detailed description of our new carnation cultivar based upon observations of greenhouse grown plants made at La Londe, France, in the Spring of 1983, the color designations being specified according to THE R.H.S. Colour Chart published by The Royal Horticultural Society of London, England.

THE PLANT

Origin: Seedling.

Parentage:

*Seed parent.*—Stock Plant No. 72 V 26.

*Pollen parent.*—Stock Plant No. 72 V 16. These unnamed varieties are individually identified in our permament records and are maintained for breeding purposes in our collection of carnation plants at La Londe, France.

Classificaton:

*Botanic.—Dianthus caryophyllus.*

*Commercial.*—Standard Carnation.

Form: Tall, erect bush, with at least four stems being emitted near the ground.

Height: Average about 100 cm. at eight months.

Main stem:

*Length.*—Less than 15 cm. due to pinching.

Branching character: The plant has a few branches.

Growth habit: Vigorous, upright and rigid.

Foliage:

*Quantity.*—Not very abundant.

*Number of leaves.*—More than 120.

*Leaf size.*—Averaging about 13 cm. long and about 1 cm. wide at the seventh node.

*Leaf shape.*—Linear with curved margins and acute tip.

*Texture.*—Leathery.

*Color.*—Upper side — 189B. Under side — 189B.

*Ribs and veins.*—Hardly noticeable.

*Rachis.*—Hardly noticeable.

THE BUD

Form: Ovoid to nearly cylindrical.

Size:

*Diameter.*—Averages about 1.8 cm.

*length.*—Averages about 3.8 cm.

Rate of opening: Normal.

Color of petals:

*When sepals first divide.*—64A.

*When petals begin to unfurl.*—64A.

Sepals:

*Number.*—Five joined at lower part and of generally acute character at the upper part with a sharp pointed apex. Sepals are hooded over the bud and when the flowers open, the sepals continue to stand up.

*Color.*—Inside — Greenish white. Outside — 139C and 144C.

*Striae.*—Longitudinal.

Calyx:

*Size.*—Medium.

*Shape.*—Bell-shaped.
*Splitting.*—The calyx rarely splits.
*Aspect.*—Smooth.

Flower stem:
*Length.*—About 75 cm.
*Character.*—Erect, strong and rather rigid.
*Color.*—189A and 189B.

THE FLOWER

Blooming habit: Recurrent and profuse during the mid-season of Spring and Fall.

Size of bloom: Medium.
*Diameter.*—Averaging about 8.7 cm.
*Depth.*—Averaging about 7.2 cm.

Borne: Singly

Shape:
*When bloom first opens.*—High centered.
*When bloom matures.*—Ball-shaped.

Petalage:
*Number of petals.*—Averages about 61.
*Arrangement.*—Imbricated.
*Form.*—Semi-circular with finely serrated edges.
*Texture.*—Soft.
*Appearance.*—Satiny.
*Color.*—Outer Petal: Body — 61A to 71B at the edges. Base — Greenish. Reverse side — 64A to 71C. Inside Petal: Body — 61A to 71B at the edges. Base — Greenish. Reverse side — 64A to 71C.

Petaloids: Less than ten.
*Size.*—Smaller than the petals.
*Color.*—The same as the petals.

Flower stem:
*Length.*—About 75 cm. (cut at tenth node).
*Character.*—Upright with very good strength.
*Color.*—189A and 189B.

Fragrance: A fragrance is present.

Persistence: The flowers hang on and dry.

Lasting quality: As a cut flower — at least ten days in vase keeping.

Disease resistance: This variety appears to be resistant to *Fusarium oxysporum* as observed INRA, Antibes, Alpes-Maritimes, France.

REPRODUCTIVE ORGANS

Stamens:
*Number.*—3 To 10.
*Arrangement.*—Encircling the pistils.
*Anthers.*—Size: Less than 4 mm. Color: Whitish.
*Filaments.*—Color — Whitish.

Pistils:
*Number.*—Two.
*Styles.*—Color — White.
*Stigma.*—Color — Lightly purplish blue.

Character of ovaries: Light green, with not very marked relief.

This new carnation variety appears to be entirely original with respect to its generally ball-shaped flowers of a solid ruby red color, which are borne on long, straight, strong stems; and by its abundant production of these flowers during its blooming season.

We claim:

1. A new carnation cultivar, substantially as herein shown and described, characterized by its ruby red flowers of medium size which bloom profusely during each of its recurrent blooming seasons, and by its vigorous growth habit which is resistant to *Fusarium oxysporum.*

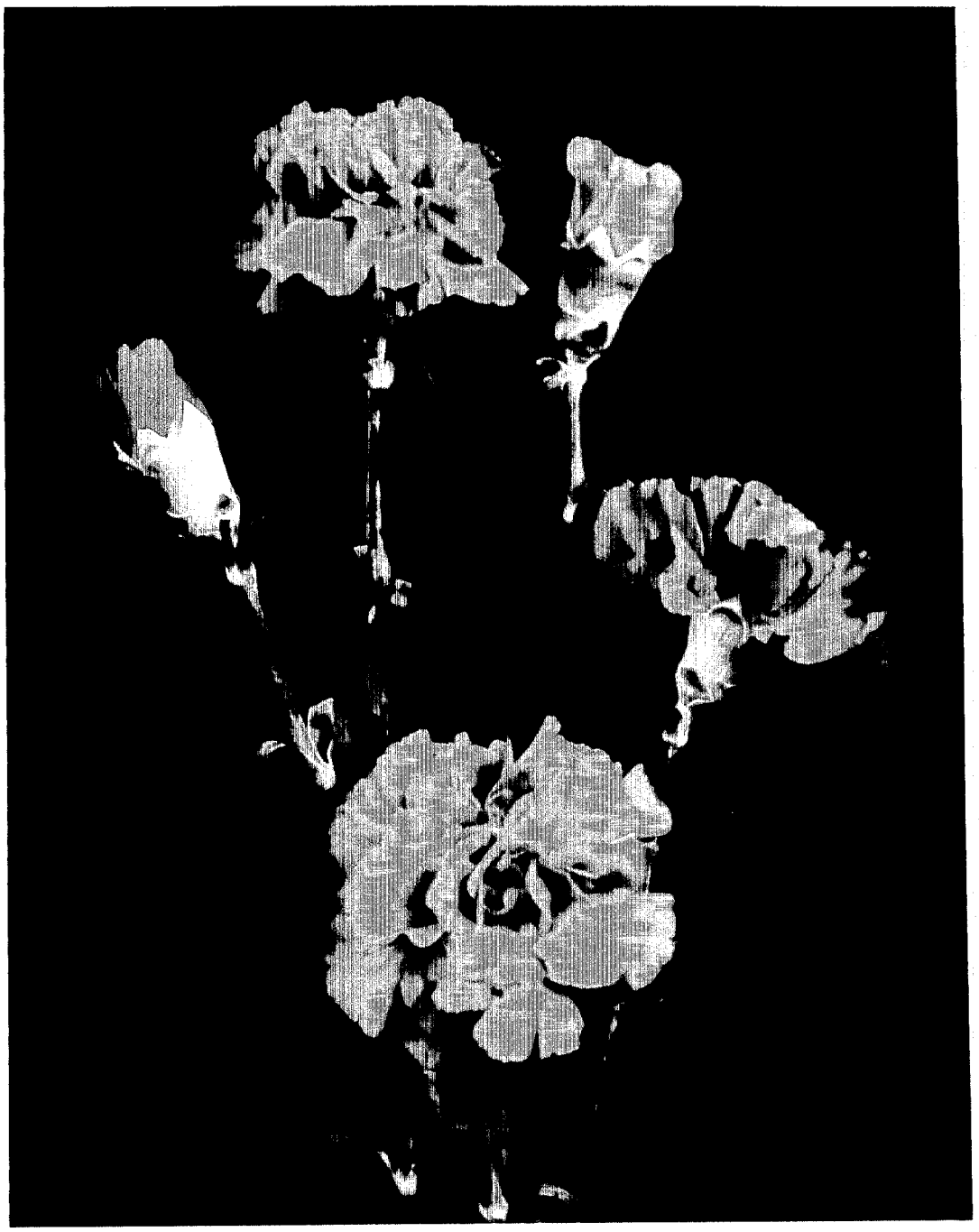

* * * * *